(12) United States Patent
Passons

(10) Patent No.: US 9,999,470 B1
(45) Date of Patent: Jun. 19, 2018

(54) ROBOTIC SURGERY MANIPULATOR

(71) Applicant: Leslie Passons, Dunlap, TN (US)

(72) Inventor: Leslie Passons, Dunlap, TN (US)

(*) Notice: Subject to any disclaimer, the term of this patent is extended or adjusted under 35 U.S.C. 154(b) by 0 days. days.

(21) Appl. No.: 14/198,638

(22) Filed: Mar. 6, 2014

Related U.S. Application Data

(60) Provisional application No. 61/787,634, filed on Mar. 15, 2013.

(51) Int. Cl.
*A61B 1/313* (2006.01)
*A61B 17/00* (2006.01)
*A61B 19/00* (2006.01)

(52) U.S. Cl.
CPC ............................... *A61B 19/2203* (2013.01)

(58) Field of Classification Search
CPC .... A61B 2218/002; A61B 2018/00291; A61B 19/2203; A61B 19/26; A61B 2019/2249; A61B 2217/005–2217/007; A61B 17/0218; A61B 2017/0225; A61M 2025/0293; A61M 25/04; A61F 2/0045; A61F 2/0063; A61F 2002/0072; A61F 2/2466; G05B 2219/45118
See application file for complete search history.

(56) References Cited

U.S. PATENT DOCUMENTS

| | | | |
|---|---|---|---|
| 2010/0256611 A1* | 10/2010 | Hansen | A61B 17/3468 606/1 |
| 2011/0067521 A1* | 3/2011 | Linn | B25J 15/0009 74/490.06 |
| 2012/0179165 A1* | 7/2012 | Grover | A61B 17/00 606/114 |

* cited by examiner

*Primary Examiner* — Joshua D Lannu
(74) *Attorney, Agent, or Firm* — Stephen J. Stark; Miller & Martin PLLC

(57) ABSTRACT

A robotic surgical manipulator provides a robotic controlled manipulator which deploys from an insertion configuration to a wider deployed configuration using two arms and a web therebetween. The web supported by the arms can then hold back a larger mass than has been previously supported by prior art techniques.

19 Claims, 4 Drawing Sheets

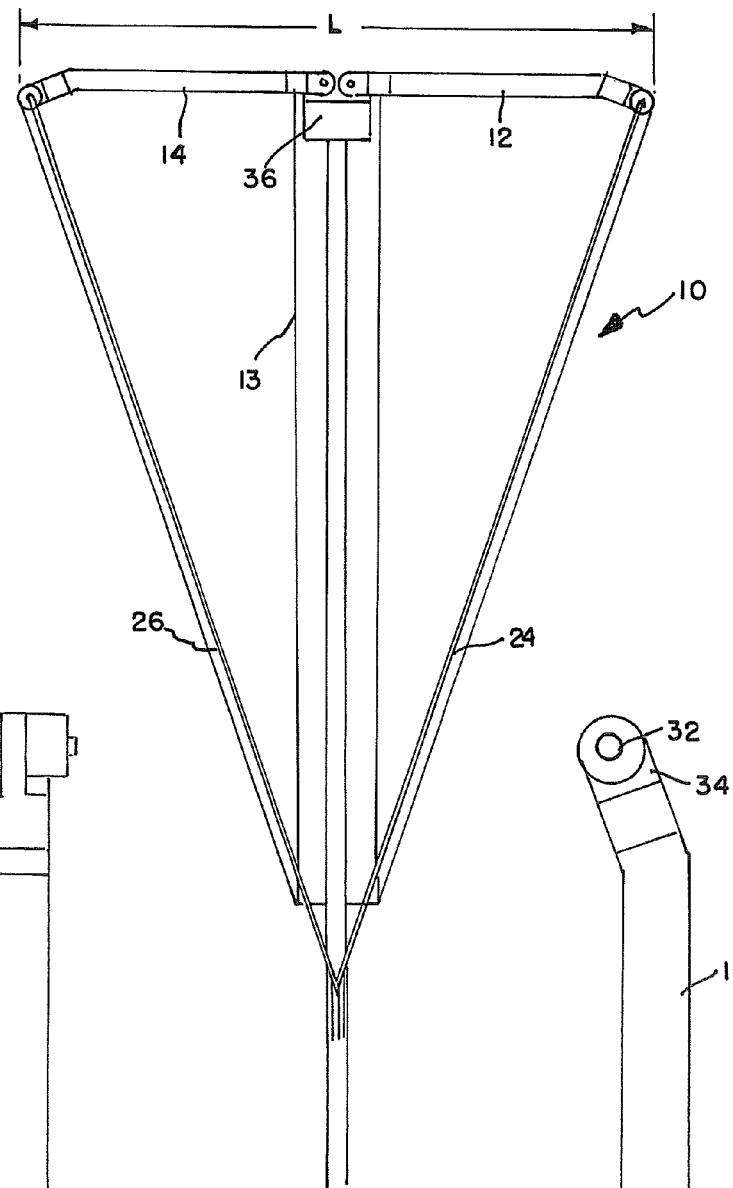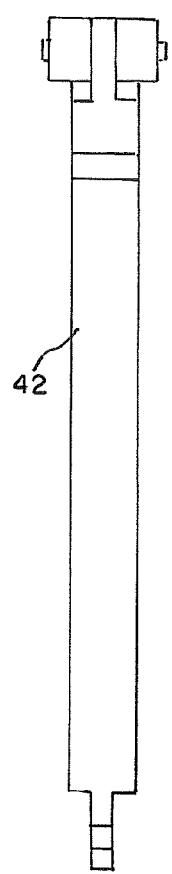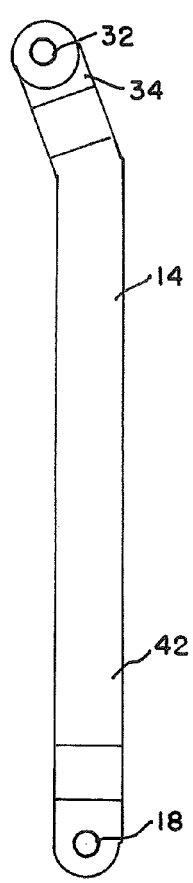
FIG. 3
FIG. 5
FIG. 6

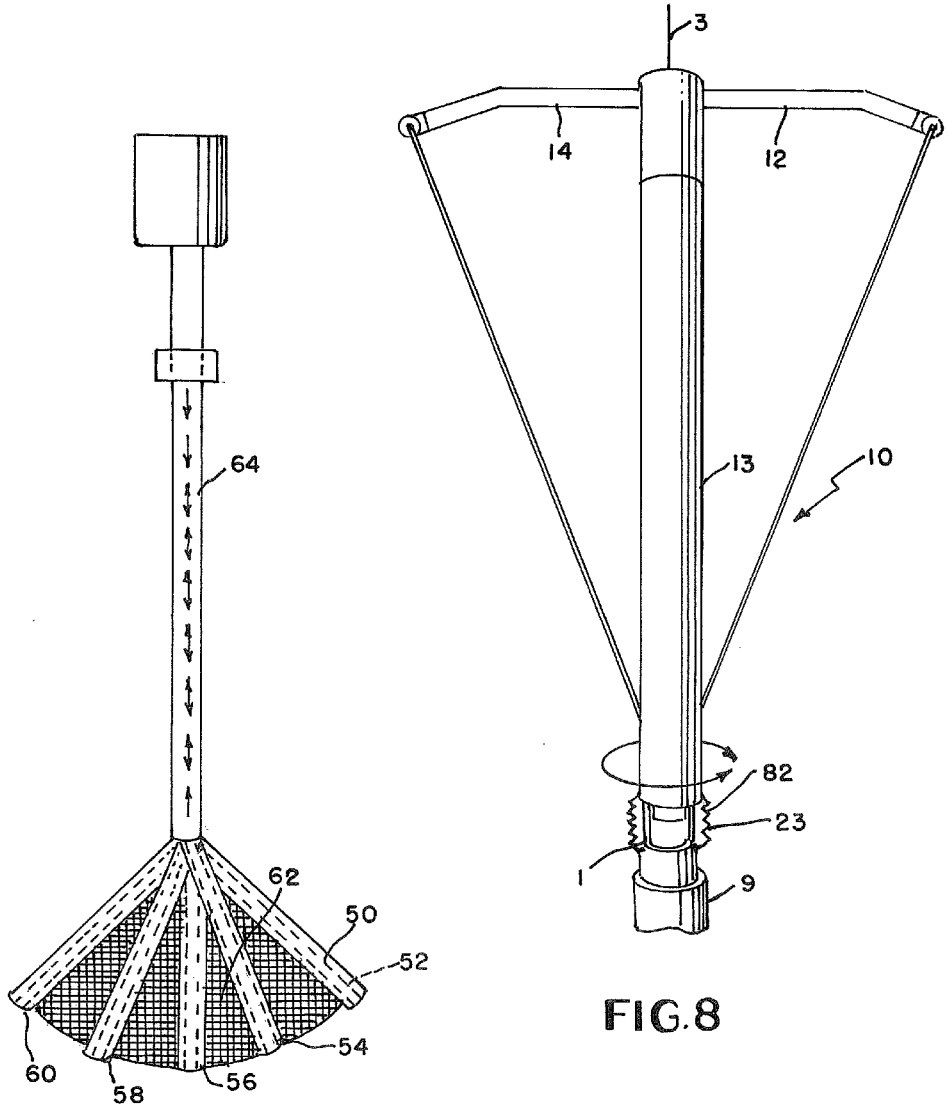

ROBOTIC SURGERY MANIPULATOR

CLAIM OF PRIORITY

This application claims the benefit of U.S. Provisional Patent Application No. 61/787,634 filed Mar. 15, 2013 which is incorporated herein by reference in its entirety.

FIELD OF THE INVENTION

The present invention relates to a manipulator for use with surgery and more particularly a manipulator for use with surgery which holds portions of the anatomy out of the way during surgical operations, preferably while still performing suction or irrigation.

BACKGROUND OF THE INVENTION

Robotic surgery has been performed for hysterectomies, prostate surgery and other procedures for many years. Companies such as Intuitive, Striker, Ethicon and others provide robotic equipment and tools for use with those procedures including robots, trocars and other devices for directing instruments into and out of the abdominal cavity for use in performing those procedures.

One common issue in some surgeries such as hysterectomies and prostate work is that the bladder or other organs and/or tissues can either obscure the view of the surgeon operating a robot or crowd the area where the doctor is working. Typically, a surgical assistant will utilize a probe suction device to push the structure out of the way such as the bladder from view. Unfortunately, the typical suction instrument often provides an elongated probe with dimensions to fit through the trocar cross section. The bladder can sometimes unfortunately migrate its way around the instrument to obscure the view or otherwise be in the way.

Accordingly, a need exists for an improved device for insertion through a trocar for surgery or other procedures to be able to use to better assist the surgeon and/or to maintain a desired field of view inside of a patient.

SUMMARY OF THE INVENTION

It is the present object of many embodiments of the present invention to provide an improved manipulator for use with surgical procedures which is particularly well adapted to be directed through trocars or other cannulated openings to then expand to a larger dimension which would not normally fit within the cross section trocar at its inserted end to then provide a web or at least a wider manipulator for moving and/or holding tissue, organs, and/or other material out of the way.

It is a present object of many embodiments of the present invention to provide an improved suction and/or irrigation device.

It is another object of many embodiments of the present invention to provide an improved device for providing an improved field of view internal to a patient during surgery techniques.

Accordingly, in accordance with a presently preferred embodiment of the present invention, a manipulator is provided which has an insertion configuration allowing the instrument to be directed through a trocar or other cannulated device such as during surgery. Once inserted, the instrument preferably has a deployed configuration in which extendable arms are extended from an insertion/retraction configuration to an extended configuration. The instrument preferably inserts through the cross section of a trocar and then is transitioned into the extended configuration whereby the inserted end fans or otherwise spreads out preferably somewhat in the shape or context of a fan, possibly having a largest width at the proximal or inserted end of the device while also possibly providing suction and/or irrigation through at least a portion of the instrument. Upon completion of use, the arms can then retract back toward the insertion configuration for removal from the body to fit through the trocar.

The preferred embodiment may be designed so that it attaches to an end of a tool provided with the Intuitive brand robot. Through activation of an internal plunger and/or pulley cables, the arms can be deployed and retracted. Cables which pull the arms to the deployed configuration to effectively spread out the fan may also be used. The cables may also assist in retraction. Twisting shaft and/or other retractions may be used for deployment and/or retraction for other embodiments. A mesh, such as a mesh bag over the arms and/or cables, can extend between the arms and a shaft. A webbed "foot" can provide a significantly wider cross section than a prior art probe as well as the cross section of the trocar so that the manipulator improve the field of view for a surgeon using the robot and/or keep structure out of the surgeon's way during procedures.

BRIEF DESCRIPTION OF THE DRAWINGS

The particular features and advantages of the invention as well as other objects will become apparent from the following description taken in connection with the accompanying drawings in which:

FIG. 3 is a top plan partially cutaway view of the manipulator of FIGS. 1-2 in a deployed configuration without the mesh installed;

FIG. 5 shows a side plan view of an arm as shown in FIG. 3;

FIG. 6 shows a top plan view of an arm as shown in FIG. 5;

FIG. 7 is a top plan view of a first preferred embodiment of the present invention;

FIG. 8 is a top plan view of the manipulator of FIGS. 1-4 with the web removed;

DETAILED DESCRIPTION OF THE PREFERRED EMBODIMENT

Figure 2:
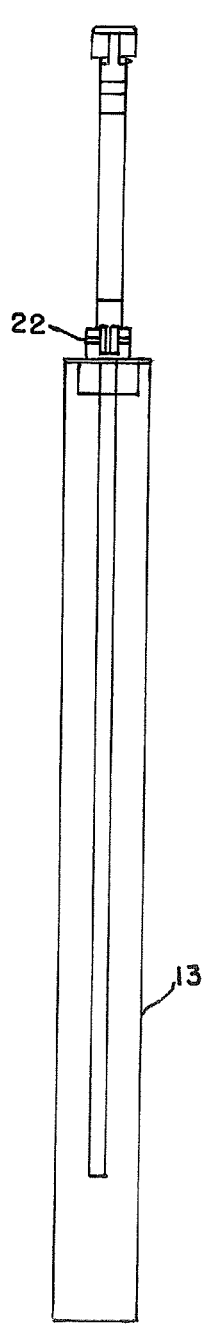
FIG. 2 is a side plan partially cutaway view of the manipulator of FIG. 1 with the cables and web removed.
Figure 1:
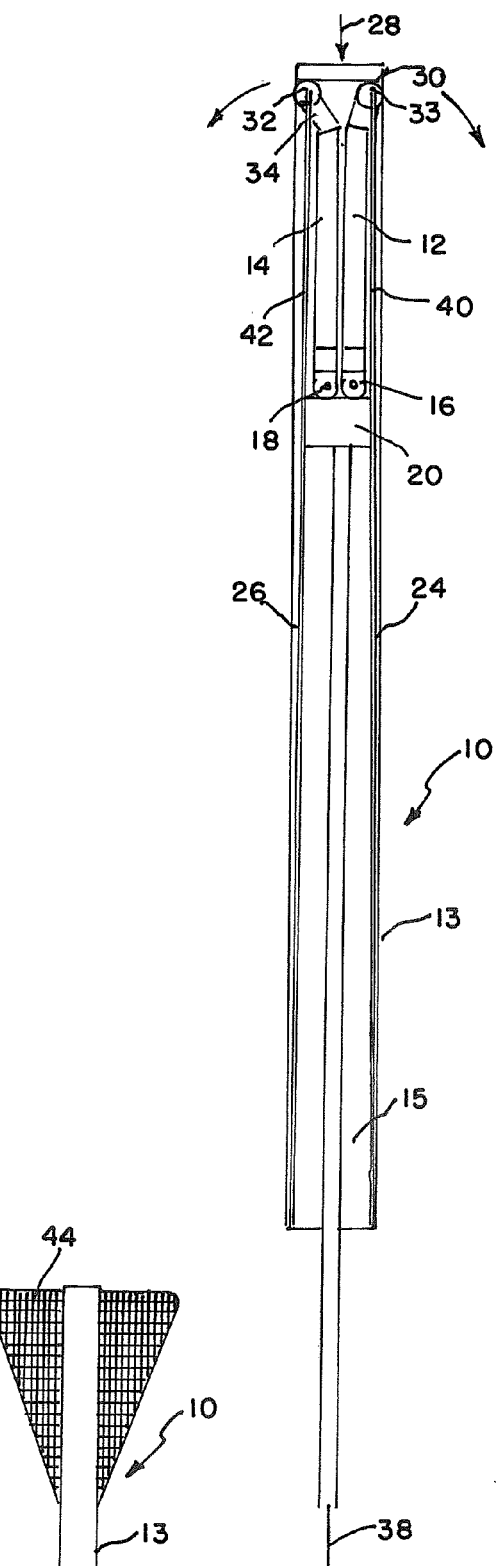
FIG. 1 is a top plan partially cutaway view of a manipulator of a presently preferred embodiment, in an insertion configuration with the web removed for clarity.

Accordingly, in accordance with a presently preferred embodiment of the present invention, FIG. 1 shows a top plan view of the presently preferred embodiment of the invention showing internals of the instrument 10 having arms 12,14 in an insertion configuration. As shown in FIG. 1, the arms 12,14 may be inserted preferably while parallel to thus providing a small enough cross section (particularly with respect to width) so as to be insertable through a trocar, catheter or other cannulated device 9. The arms 12,14 may connect at spaced apart pivots 16,18 to at boss 22 which connects to base 20 as shown in FIGS. 1 and 2. Pivots pivot along at least one foot two or more arm pivot axes 7,5 which are shown as parallel and spaced apart in the figures. Insertion axis 3 (extending through cannulated device 9) is shown perpendicular to one or more arm pivot axes in the preferred embodiment.

FIG. 2 shows the structure without the cables 24,26 connected at the inserted proximal end 28 to the arms 12,14 at their proximal ends 28. Receivers 30,32 preferably receive the cables 24,26 and preferably provided on a direction on offsets 34,36. Offsets 34,36 preferably extend laterally to the arm at least somewhat so that when the cables 24,26 are pulled in a direction of the operational axis 38 which may or may not be the insertion axis 3 after initial entry into a body, the arms 12,14 preferably deploy to the deployed configuration as shown in FIG. 3. FIG. 3 preferably illustrates a maximum deployed configuration such as by having the arms 12,14 contact base 20 towards the proximal end 28 of the base 36 at the maximum deployed configuration to present further rotation of the arms 12,14 about pivots 16,18. This configuration may utilize the cables 24,26 to at least assist in spreading out the arms (and connected mesh or web 44 if utilized) to provide an at least somewhat fan like shape with the largest distance L preferably disposed towards the proximal end 28 in the deployed configuration. Depending on the relative stiffness of the cables 24,26, they can be used to return the manipulator 12 back to its insertion configuration as well.

Offset 33,34 preferably directs the arms 12,14 in the lateral direction which is defined as perpendicular to the operation axis 38 or the axis of insertion of the instrument 10. Operation axis 38 may also be a rotation axis for at least some embodiments. The offsets 33,34 preferably meet at an angle relative to the extension portions 40,42 which may preferably connect directly to the pivots 16,18. The extension portions 40,42 may preferably be parallel to one another in the insertion configuration shown in FIG. 1 and are nonparallel or even collinear as shown in FIG. 3 in the deployed configuration.

Figure 4:
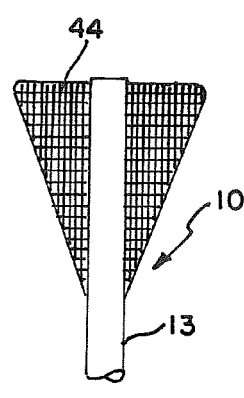
FIG. 4 is a top plan view similar to FIG. 3 with the mesh installed.

FIGS. 1-3 do not show the web 44 attached which is shown in FIG. 4 which provides a web or a net to provide wider cross section L other than just at arms 12,14. Mesh 44 can extend over cables 24,26 and/or otherwise at least partially intermediate arms 12,14 although some embodiments may be constructed differently such as the embodiment of FIG. 7 which could provide a series of arms 50, some of which may have suction and/or irrigation ports 52 provided therewith. This embodiment may also deploy to a fan configuration. Webbing such as between adjacent arms such as arms 50,54,56,58,60 can also include web 62 relative to shafts 64. Arms may be deployable in various ways as is known in the art. One inserted through the trocar and then retracted for removal.

Upon retraction, the trocar or other cannulated opening 9, may assist if cables 24,26 are not used to push arms 12,14 back to the insertion configuration when withdrawing the instrument 10 from the trocar. Rotation of shaft 13 or other component(s) may also assist in this process. There are various ways the areas could be made to deploy and then retract. The width L is preferably at least twice as wide as width W of the shaft 13 which must be no wider than the width of the internal diameter of the trocar of other cannulated opening through which it is inserted in the inserted configuration. As the cables 24,26 spread the arms 12,14 out, they preferably assist with the arms 12,14 in deploying the web 44 between the arms 12,14 and the shaft 13 and the cables 24,26 if utilized. The illustrated web 44 is somewhat triangular shaped, but other embodiments may have other shapes. The web 44 and/or deployed arms 12,14 preferably have a width L greater than W when in the deployed configuration and less than W with the arms 12,14 in the insertion configuration. In fact, the length L is preferably at least 2, at least 3, at least 4, at least 5 and even up to at least 7 or more times greater than W at the proximal end than W and can taper down to W as one proceeds away from the proximal end 28 or other direction depending on the configuration chosen.

The arms 12,14 and shaft 13 and other components may be stainless steel and/or other appropriate materials. The mesh 44 may be Rayon™ or other appropriate material. The mesh 44 is preferably anchored at least partially internal to or at least to the shaft 13 to ensure it is removed with the manipulator 10 when removed from use and may be secured as desired to other structure of the manipulator such as the arms 12,14 and/or cables 24,26. The mesh 44 may be deployed from at least partially internal to the shaft 13 from the insertion configuration to the deployed configuration. Flexible cover 19 may be useful to protect platform pivot 21 disposed along platform pivot axis (which may be perpendicular to and/or offset from the at least one arm axis 5,7).

Although the preferred embodiment fans out at the proximal end such as at least 90° if not all 90°, other configurations could fan out at a location spaced from and even in a direction away from the proximal end 28 either towards or away from the proximal end 28. Internal to shaft 13 suction and/or irrigation may be at least selectively supplied such as from a robot arm and/or other tool or structure such as through conduit 1 or otherwise at least in the deployed configuration.

In use, the deployed tool provides a larger width L as well as cross sectional capability to assist in holding structures out of either the field of view or out of the way over than prior art probes.

FIG. 8 is useful to show that the shaft 13 can rotate even once inserted and the arms 12,14 could also be moved even once inserted between the extended configuration and the insertion/retraction configuration for at least some embodiments. In fact, rotation of the shaft 13 may extend the deployment and/or retraction of the arms 12,14 from a particular embodiment. By being able to move the arms 12,14, the mesh 44 can also be moved as would be understood by those of ordinary skill in the art which may assist in operator even and/or holding structure out of the way and/or out of the field of view during surgical techniques.

Figure 9:
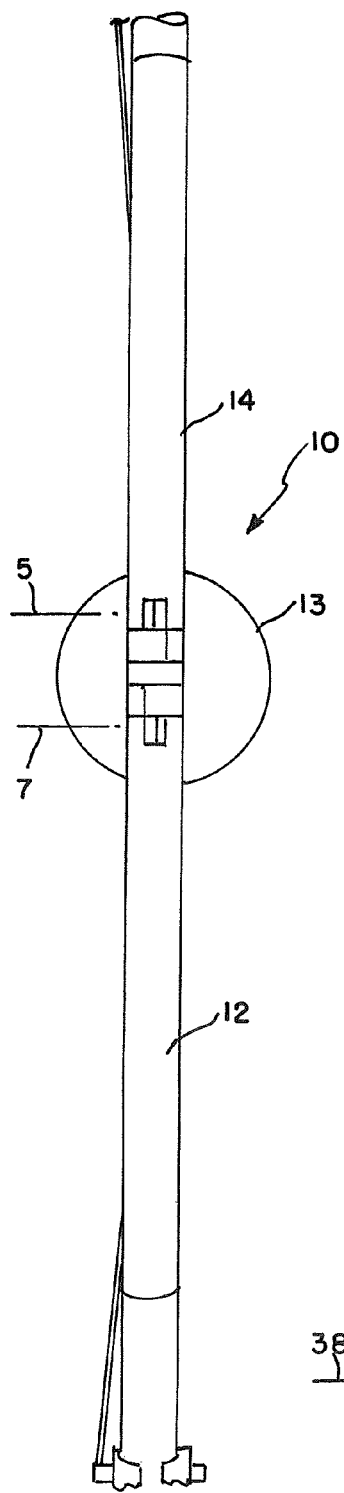
FIG. 9 is a front and plan view of the manipulator of FIGS. 1-4 with the web removed.
Figure 10:
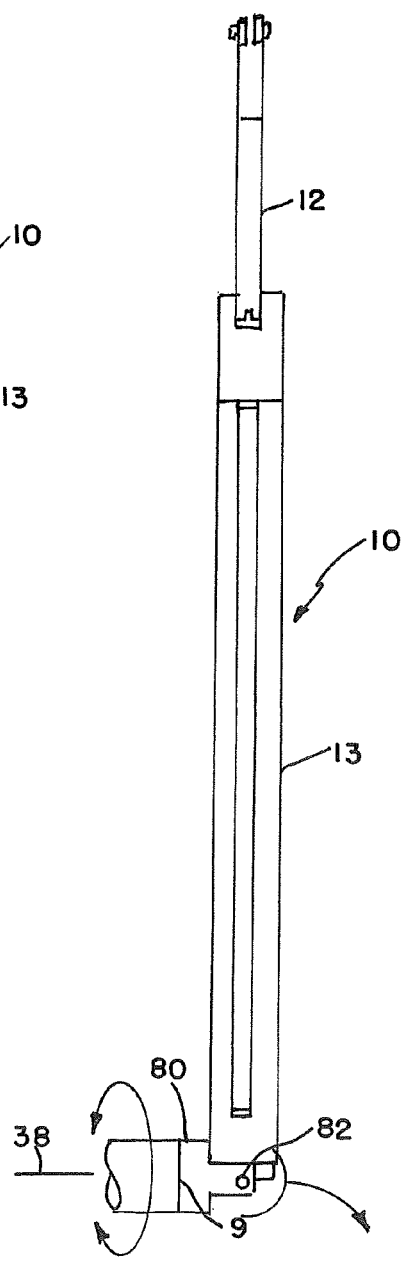
FIG. 10 is a side plan view of the structure of FIG. 9.

FIG. 9 also shows a front view of the manipulator 10. FIG. 10 shows a side plan view. In this embodiment, a platform 80 is utilized to attach to an operator such as an extension, a tool and/or a robot and is provided a pivot 82 along platform pivot axis 23 relative to shaft 13. It may be that the cables running through the shaft 13 or other device may allow for the rotation of the shaft 13 relative to the platform 80 to assist in moving the shaft 13. The arms 12,14 may also move relative to the shaft 13 and can be directed up to and perpendicular to the insertion axis 38. Insertion axis 38 may also be a rotation axis of platform 80 and/or shaft 13. The length of shaft 13 may be selected based on the surgical procedures to be performed and the desired placement of the arms 12,14 and web 44.

Figure 11:
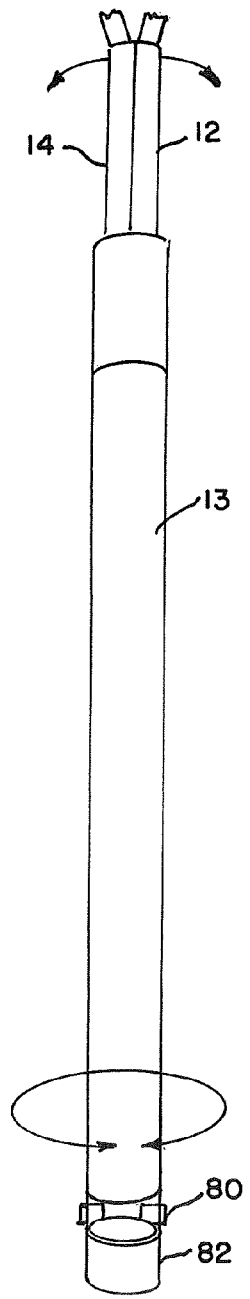
FIG. 11 is a top plan view showing retraction of the arms for at least some embodiments.

It is anticipated that shaft 13 may be returned to the insertion configuration 38 for retrieval of the manipulator 10. As is shown in FIG. 11, rotation of shaft 13 and/or withdrawal of the arms 12,14 with cables or otherwise can pull the arms into shaft 13 to assist in insertion and/or withdrawal for at least some insertion configurations. It may be possible for rotation of the shaft 13 or other mechanism(s) to drive internal devices to assist in deployment and/or withdrawal. Cables 24,26 may be utilized for at least some embodiments.

Although shaft 13 could be a fixed length, it may be extendable in order to extend and/or retract at least to a degree for various procedures. Threaded rod 15 and/or cables could be used as could be understood by those of ordinary skill in the art.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A robotic surgical manipulator comprises:
   a base directed through a cannulated device providing a cannulated passage into a human body, said base having first and second arms pivotably connected thereto and at least partially supporting a web extending intermediate the first and second arms in a deployed configuration, said base inserted through an insertion axis extending linearly through the cannulated device in an insertion configuration, and said first and second arms pivoting along at least one arm pivot axis to the deployed configuration,
   when in the insertion configuration, said manipulator having an insertion width allowing the manipulator to pass through the cannulated passage along the insertion axis of less than a width of the cannulated passage; and
   when in the deployed configuration, said first and second arms have distal ends extending at least two times the insertion width to form a paddle with the web, with said first and second arms extending which would prevent the manipulator from being removed from the cannulated passage until returned to the insertion configuration;
   a shaft connected to the base, said shaft pivotably connected at a pivot spaced from the base to a platform having a platform pivot axis whereby when in the deployed configuration the base and arms exit the cannulated device and whereby the shaft is rotated about the pivot to be angled with the paddle, to be non-colinear with the insertion axis.

2. The robotic surgical manipulator of claim 1 wherein when in the deployed configuration, said first and second arms have distal ends extending at least three times the insertion width.

3. The robotic surgical manipulator of claim 2 wherein when in the deployed configuration, said first and second arms have distal ends extending at least four times the insertion width.

4. The robotic surgical manipulator of claim 3 wherein when in the deployed configuration, said first and second arms have distal ends extending at least five times the insertion width.

5. The robotic surgical manipulator of claim 4 wherein when in the deployed configuration, said first and second arms have distal ends extending at least seven times the insertion width.

6. The robotic surgical manipulator of claim 1 wherein at least a portion of the web is located within the shaft in the insertion configuration.

7. The robotic surgical manipulator of claim 1 wherein the web extends from the shaft to the first and second arms in the deployed configuration.

8. The robotic surgical manipulator of claim 1 wherein the web is disposed at least partially internal to the shaft in the insertion configuration.

9. The robotic surgical manipulator of claim 1 wherein one of suction and irrigation is selectively directed through the shaft in the deployed configuration.

10. The robotic surgical manipulator of claim 1 further comprising a cable operably coupled to the shaft, said cable at least assisting in pivoting the shaft relative to the platform at the platform pivot.

11. The robotic surgical manipulator of claim 10 wherein the at least one arm pivot axis and platform pivot axis are perpendicular and spaced apart relative to one another.

12. The robotic surgical manipulator of claim 1 wherein the first and second arms pivot up to 90 degrees, respectively between the insertion and the deployed configurations.

13. The robotic surgical manipulator of claim 1 wherein the web is non-rigid and the first and second arms provide an outer periphery to support the web.

14. A robotic surgical manipulator comprises:
   a cannulated device configured to be inserted into a human body;
   a base having first and second arms pivotably connected thereto;
   a web extending at least partially intermediate the first and second arms in a deployed configuration;
   wherein said base is inserted through an insertion axis in an insertion configuration, when in the insertion configuration, said manipulator having an insertion width allowing the manipulator to pass through a cannulated passage created by the cannulated device along the insertion axis of less than a width of the cannulated passage; and
   when in the deployed configuration, said first and second arms have distal ends extending at least two times the insertion width which would prevent the manipulator from being removed from the cannulated passage until returned to the insertion configuration, said arms and web forming a paddle for use in surgical procedures;
   a shaft operably coupled to the base, said shaft having a conduit therethrough receiving at least one of suction and irrigation therethrough; and
   at least one cable extending through the cannulated passage operably coupled to the shaft at least assisting in coordinating movement of the paddle relative to the cannulated device in a direction non-colinear with the insertion axis.

15. The robotic surgical manipulator of claim 14 wherein said first and second arms pivot along at least one arm pivot axis perpendicularly oriented relative to the insertion axis.

16. The robotic surgical manipulator of claim 15 wherein the base is connected by the shaft to a platform.

17. The robotic surgical manipulator of claim 16 wherein the at least one of suction and irrigation is selectively directed through the shaft past the platform.

18. The robotic surgical manipulator of claim 16 wherein the shaft is connected at a platform pivot to the platform, and the platform pivot is oriented along a platform pivot axis, said platform pivot axis oriented perpendicularly to the at least one arm pivot axis, and the shaft exits the cannulated device and the shaft rotates at the platform pivot to be non-colinear relative to the insertion axis.

19. The robotic surgical manipulator of claim 15 wherein the at least one arm pivot axis comprises two spaced apart arm pivot axes operably coupled respectively to the first and second arms at the base.

\* \* \* \* \*